(12) United States Patent
Nazir et al.

(10) Patent No.: US 11,713,287 B2
(45) Date of Patent: Aug. 1, 2023

(54) ENERGY EFFICIENT STEAM CRACKING PROCESS

(71) Applicant: SABIC GLOBAL TECHNOLOGIES B.V., Bergen op Zoom (NL)

(72) Inventors: Muhammad Kashif Nazir, Jubail Industrial (SA); Ahmad J. Al-Rebeh, Jubail Industrial (SA); Omar Hassan Al-Amoudi, Jubail Industrial (SA); Saud S. Jebreen, Jubail Industrial (SA)

(73) Assignee: SABIC GLOBAL TECHNOLOGIES B.V., Bergen op Zoom (NL)

( * ) Notice: Subject to any disclaimer, the term of this patent is extended or adjusted under 35 U.S.C. 154(b) by 0 days.

(21) Appl. No.: 17/760,457

(22) PCT Filed: Feb. 11, 2021

(86) PCT No.: PCT/IB2021/051141
§ 371 (c)(1),
(2) Date: Aug. 10, 2022

(87) PCT Pub. No.: WO2021/161219
PCT Pub. Date: Aug. 19, 2021

(65) Prior Publication Data
US 2023/0134731 A1 May 4, 2023

Related U.S. Application Data

(60) Provisional application No. 62/976,984, filed on Feb. 14, 2020.

(51) Int. Cl.
*C10G 9/36* (2006.01)
*C07C 5/327* (2006.01)

(52) U.S. Cl.
CPC .................... *C07C 5/327* (2013.01)

(58) Field of Classification Search
CPC .......... B01J 19/0026; B01J 2219/00252; B01J 2219/00247; C10G 9/36; C10G 9/16;
(Continued)

(56) References Cited

U.S. PATENT DOCUMENTS 6,740,791 B2   5/2004   Kuechler et al.
7,699,596 B2   4/2010   Garcia
(Continued)

FOREIGN PATENT DOCUMENTS

CN     101967077 A      2/2011
KR     20150057266 A    5/2015
WO     WO2001004236 A1  1/2001

OTHER PUBLICATIONS

Neelis et al. "Energy Efficiency Improvement and Cost Saving Opportunities for the Petrochemical Industry." An Energy Star Guide for Energy and Plant Managers. Energy Analysis Department, Environmental Energy Technologies Division, Ernest Orlando Lawrence Berkeley National Laboratory. Berkeley, California. Jun. 2008. 133 pages.

(Continued)

*Primary Examiner* — Sharon Pregler
(74) *Attorney, Agent, or Firm* — Norton Rose Fulbright US LLP

(57) ABSTRACT

A method for steam cracking of a hydrocarbon feed is disclosed. The method can include heating a hydrocarbon feed stream with a first quench water stream to form a heated hydrocarbon feed stream and a second quench water stream having a temperature lower than the first quench water stream, steam cracking the heated hydrocarbon feed stream to form a cracked stream comprising cracked gases, contacting the cracked stream with a quench water to form a gaseous stream comprising quenched cracked gases and a crude water stream comprising heated quench water and (Continued)

pyrolysis gasoline, and separating the crude water stream to form the first quench water stream.

20 Claims, 4 Drawing Sheets

(58) Field of Classification Search
CPC .......... C10G 9/002; C10G 75/00; C10G 7/04; C10G 2400/02; C10G 2300/4075; B01D 17/0214; B01D 17/0211; B01D 19/0042; C02F 2101/32; C02F 2103/365; C02F 2001/007

See application file for complete search history.

(56) References Cited

U.S. PATENT DOCUMENTS

| | | |
|---|---|---|
| 2006/0149115 A1 | 7/2006 | Foral et al. |
| 2019/0375992 A1* | 12/2019 | Karime ................ B01J 19/0026 |
| 2020/0024525 A1 | 1/2020 | Dijkmans et al. |
| 2022/0340822 A1* | 10/2022 | Rooney .................... C10G 9/20 |

OTHER PUBLICATIONS

International Search Report and Written Opinion from PCT/IB2021/051141 dated Apr. 19, 2021, 10 pages.

* cited by examiner

ENERGY EFFICIENT STEAM CRACKING PROCESS

CROSS REFERENCE TO RELATED APPLICATIONS

This application is a national phase application under 35 U.S.C. § 371 of International Application No. PCT/IB2021/051141 filed Feb. 11, 2021, which claims priority to U.S. Provisional Patent Application No. 62/976,984 filed Feb. 14, 2020. The entire contents of each of the above-referenced disclosures is specifically incorporated by reference herein without disclaimer.

BACKGROUND OF THE INVENTION

A. Field of the Invention

The invention generally concerns systems and processes for steam cracking of hydrocarbons. In particular, the invention concerns systems and processes for steam cracking of a hydrocarbon feed, where the hydrocarbon feed prior to steam cracking is heated with a heated quench water produced from quenching a steam cracking reaction.

B. Description of Related Art

Alkenes are important petrochemical products with a continuously growing demand. Light alkenes, such as ethylene and propylene, are usually produced by steam cracking of petroleum-based feedstocks, such as naphtha, liquid petroleum gas, ethane or propane. In conventional steam cracking (pyrolysis) process a hydrocarbon feed is preheated with steam and the preheated hydrocarbon feed in presence of steam is further heated to 750° C. to 900° C. to crack the hydrocarbon feed. The hot cracked hydrocarbons produced from steam cracking of the hydrocarbon feed are then quenched to minimize unwanted reactions and to optimize desired product yield. The hot cracked hydrocarbons are contacted with a quench water in the quench tower to quench the hot cracked hydrocarbons. The heated quench water is cooled down by cooling water and recycled back to the quench tower as a part of the continuous quenching process of the hot cracked hydrocarbon. This typical steam cracking process is an energy consuming process. Substantial energy is required for pre-heating the hydrocarbon feed, cooling the heated quench water, and ultimately cracking the hydrocarbons in the feed stream.

An attempt to provide a solution to this energy consumption is disclosed in WO2001004236A1. This publication discloses a method for steam cracking of hydrocarbons. A pre-heated mixture of hydrocarbons and water vapor is heated to a desired temperature to crack the hydrocarbons and form olefins. The energy source required for pre-heating the hydrocarbon mixture and cracking is supplied by a cogeneration system which produces by combustion of a fuel both thermal and mechanical energy transformed into electricity. The hydrocarbons mixture is first subjected to pre-heating by the thermal energy supplied by cogeneration, and then heated to the desired cracking temperature by electric heating using the electricity supplied by cogeneration. However this method uses additional external energy from fuel combustion to pre-heat the hydrocarbon feed.

SUMMARY OF THE INVENTION

A discovery has been made that provides a solution to at least one of the aforementioned problems associated with high energy consumption during steam cracking of hydrocarbons. The solution can include pre-heating a hydrocarbon feed for steam cracking by heat exchange with a heated quench water produced from quenching a steam cracking reaction. External energy consumption can be reduced by pre-heating the hydrocarbon feed with the heated quench water instead of using an external energy source. Further, the heated quench water can also be cooled in the heat exchange process, requiring comparatively less external energy to cool the heated quench water when compared with a typical process that uses cooled water to reduce the temperature of heated quench water. For example, the energy needs to produce the cooled water can be reduced or avoided all together with the processes of the present invention.

In one aspect of the present invention, a method for steam cracking of a hydrocarbon feed is described. The method can include any one of, any combination of, or all of steps (a)-(d). In step (a) a hydrocarbon feed stream can be heated with a first quench water stream to form a heated hydrocarbon feed stream and a second quench water stream. The heated hydrocarbon feed stream can be formed from thermal energy transfer from the first quench water stream to the hydrocarbon feed stream. This thermal energy transfer can result in the second quench water stream, which can have a temperature lower than the first quench water stream. The heating of the hydrocarbon feed and cooling of the first quench water stream can be performed without the use of any additional energy input (e.g., heating or cooling elements, heated dilution streams, cooled water streams, etc.). In other instances, however, addition energy input can also be used in combination with the processes of the present invention. In step (b) a cracked stream containing cracked gases can be formed by steam cracking of the heated hydrocarbon feed stream. In step (c) the cracked stream can be contacted with a quench water (e.g., quench water in a quench water tower) from a quench water stream to form a gaseous stream containing quenched cracked gases and a crude water stream containing heated quench water. In step (d) the crude water stream can be separated to form the first quench water stream. The first quench water stream can contain the heated quench water separated from the crude water stream. Steam cracking in step (b) can include contacting the heated hydrocarbon feed stream with a dilution steam stream to form a mixed stream, and heating the mixed stream under conditions sufficient to steam crack at least a portion of the hydrocarbons present in the mixed stream and form the cracked stream. In some aspects, the crude water stream can further include condensed and/or liquid hydrocarbons and in step (d) the heated quench water can be separated from the at least a portion of the condensed and/or liquid hydrocarbons to form the first quench water stream. In certain aspects, the condensed and/or liquid hydrocarbons can contain pyrolysis gasoline and/or tar. In some aspects, the first quench water stream can have a temperature of 70 to 120° C., and preferably from 76 to 84° C. In some aspects, the second quench water stream can have a temperature of 50 to 100° C., and preferably 78 to 83.5° C. The second quench water stream can contain partially cooled quench water formed by heat transfer from the heated quench water. In some aspects, the heated hydrocarbon feed stream can have a temperature of 50° C. to 100° C., and preferably from 70° C. to 80° C. In some aspects, the second quench water stream can be cooled down further by quench water coolers using cooling water as a cooling media to form the quench water stream. In some aspects, the quench water stream can have a temperature of 20° C. to 70° C., and preferably from 35° C. to 42° C. The quench water stream can contain quench water i.e. cold quench water formed by heat transfer from the partially cold quench water. The hydrocarbon feed stream can be heated with the first quench water stream by a heat exchanger with and/or without direct contact. In some aspects, the hydrocarbon feed stream can be heated with the first quench water stream without direct contact. The temperature of the heated hydrocarbon feed stream can be higher, such as 5° C. to 85° C., and preferably from 40° C. to 75° C., higher compared to the hydrocarbon feed stream. In some aspects, the temperature of the second quench water stream can be 0.5 to 70° C., preferably 5 to 70° C., and more preferably 0.5 to 1.5° C. lower compared to the first quench water stream. In some aspects, the cracked stream can be contacted with the quench water in a quench water tower. In some aspects, the crude water stream can be separated to form the first quench water stream in a quench water separator drum (the term "drum" also includes containers).

In some aspects, the heated hydrocarbon feed stream prior to steam cracking and prior to contacting with a dilution steam stream can be heated with a low pressure steam stream to form a second heated hydrocarbon feed stream, and the second heated hydrocarbon feed stream can be steam cracked in step (b). The second heated hydrocarbon feed stream can be steam cracked in step (b) by contacting the second heated hydrocarbon feed stream with the dilution steam stream to form the mixed stream, and heating the mixed stream under conditions sufficient to form the cracked stream. In some aspects, the low pressure steam stream can have a pressure of from 0.1 to 2 MPa, preferably 0.35 to 0.45 MPa, and/or a temperature of from 220° C. to 280° C. In some aspects, the second heated hydrocarbon feed stream can have a temperature of 100 to 250° C., and preferably from 70 to 80° C. The temperature of the second heated hydrocarbon feed stream can be higher, such as 5 to 150° C., and preferably from 40 to 75° C. higher compared to the heated hydrocarbon feed stream. The heated hydrocarbon feed stream can be heated with the low pressure steam stream by a heat exchanger with and/or without direct contact. In some aspects, prior to steam cracking and contacting with the dilution steam stream the second heated hydrocarbon feed stream can be further heated with a high pressure steam stream to form a third heated hydrocarbon feed stream and the third heated hydrocarbon feed stream can be steam cracked in step (b). The third heated hydrocarbon feed stream can be steam cracked in step (b) by contacting the third heated hydrocarbon feed stream with the dilution steam stream to form the mixed stream, and heating the mixed stream under conditions sufficient to form the cracked stream. In some aspects, the high pressure steam stream can have a pressure of 1.5 to 5 MPa, and preferably 4 to 4.5 MPa and/or temperature of 370° C. to 390° C. In some aspects, the third heated hydrocarbon feed stream can have a temperature of from 130° C. to 400° C., preferably from 200° C. to 400° C., and more preferably from 130° C. to 145° C. The second heated hydrocarbon feed stream can be heated with the high pressure steam stream by a heat exchanger with and/or without direct contact. The temperature of the third heated hydrocarbon feed stream can be higher, such as from 5° C. to 200° C., and preferably from 8° C. to 15° C. higher compared to the second heated hydrocarbon feed stream. The steam cracking in step (b) can be performed in a cracking furnace. In some aspects, the heated hydrocarbon feed stream or the second heated hydrocarbon feed stream or the third heated hydrocarbon feed stream can be fed to a convection section of the cracking furnace and can get further heated and the further-heated heated hydrocarbon feed stream or second heated hydrocarbon feed stream or third heated hydrocarbon feed stream can be contacted with the dilution steam stream to form the mixed stream. In some aspects, the mixed stream can be heated in a radiation section of the cracking furnace to steam crack at least a portion of the hydrocarbons present in the mixed stream and form the cracked stream. In some aspects, the steam cracking can be performed at a temperature 700° C. to 1000° C., or preferably from 820° C. to 900° C. and/or a of pressure 0.05 MPa to 0.1 MPa. The hydrocarbon to steam weight ratio in the mixed stream can be 0.3 to 0.4. The hydrocarbon feed stream can contain one or more hydrocarbons, such as naphtha, liquid petroleum gas (LPG), ethane or propane or any combination thereof. In some aspects, the quenched cracked gases can contain olefins such as ethylene, propylene, and/or butylene. The hydrocarbon feed stream can optionally contain a heavy hydrocarbon feed.

One aspect of the present invention is directed to a system for steam cracking of a hydrocarbon feed. The system can include a cracking furnace, a quench water tower, quench water separator, a first heat exchanger, and a quench water cooler. The first heat exchanger can be configured to receive (i) a first quench water stream from the quench water separator and (ii) a hydrocarbon feed stream. The first heat exchanger can be configured to perform thermal energy exchange between the hydrocarbon feed and the first quench water stream such that the temperature of the hydrocarbon feed is increased and the temperature of the first quench water stream is reduced. This thermal energy exchange can be performed with or without direct contact between the hydrocarbon feed and the first quench water stream. A result of this thermal energy exchange is the formation of a heated hydrocarbon feed stream having a temperature higher than the hydrocarbon feed stream and a second quench water stream having a temperature lower than the first quench water stream. The quench water cooler can be configured to receive the second quench water stream from the first heat exchanger and cool, e.g. decrease temperature of the second quench water stream, to form a quench water stream. The quench water cooler can include cooled water having a temperature lower than the second quench water stream such that a thermal energy transfer occurs, which results in the second quench water stream having a lower temperature and the cooled water having a higher temperature. The thermal energy transfer between the second quench water stream and cooled water can occur with and/or without direct contact between them. In some instances, the cooled water can be directly contacted with the second quench water stream. In some other instances, thermal energy transfer between the second quench water stream and cooled water can occur without direct contact between them. The cracking furnace can be configured to receive the heated hydrocarbon feed stream from the first heat exchanger and crack the heated hydrocarbon feed stream, e.g. crack at least a portion of the hydrocarbons present in the heated hydrocarbon feed stream, to form a cracked stream containing cracked gases. In some aspects, prior to steam cracking the heated hydrocarbon feed stream can be contacted with a dilution steam to form a mixed stream and the cracking furnace can be configured to receive the mixed stream and crack at least a portion of the hydrocarbons present in the mixed stream, to form the cracked stream. The quench water tower can be configured to (i) receive the cracked stream from the cracking furnace and (ii) the quench water stream containing quench water i.e. quench water from the quench water cooler. The quench water tower can be configured to contact the cracked stream with the quench water to form a gaseous stream containing quenched cracked gases (e.g., ethylene, propylene, butylene, preferably at least ethylene) and a crude water stream containing heated quench water and condensed and/or liquid hydrocarbons. The quench water separator can be configured to receive the crude water stream and separate the heated quench water from the condensed and/or liquid hydrocarbons to form the first quench water stream containing the heated quench water.

In some aspects, the system can further include a second heat exchanger. The second heat exchanger can be operatively positioned e.g., connected between the first heat exchanger and the cracking furnace. The second heat exchanger can be configured to receive the heated hydrocarbon feed stream from the first heat exchanger and a low pressure steam stream, and heat the heated hydrocarbon feed stream with the low pressure steam stream with or without direct contact to form a second heated hydrocarbon feed stream. The second heated hydrocarbon feed stream can be contacted with the dilution steam to form the mixed stream and the cracking furnace can be configured to receive the mixed stream and crack at least a portion of the hydrocarbons present in the mixed stream, to form the cracked stream.

In some aspects, the system can further include a third heat exchanger. The third heat exchanger can be operatively positioned, e.g., connected between the second heat exchanger and the cracking furnace. The third heat exchanger can be configured to receive the second heated hydrocarbon feed stream from the second heat exchanger and a high pressure steam stream, and heat the second heated hydrocarbon feed stream with the high pressure steam stream with or without direct contact to form a third heated hydrocarbon feed stream. The third heated hydrocarbon feed stream can be contacted with the dilution steam to form the mixed stream and the cracking furnace can be configured to receive the mixed stream and crack at least a portion of the hydrocarbons present in the mixed stream, to form the cracked stream.

Other embodiments of the invention are discussed throughout this application. Any embodiment discussed with respect to one aspect of the invention applies to other aspects of the invention as well and vice versa. Each embodiment described herein is understood to be embodiments of the invention that are applicable to other aspects of the invention. It is contemplated that any embodiment discussed herein can be implemented with respect to any method or composition of the invention, and vice versa. Furthermore, compositions and systems of the invention can be used to achieve methods of the invention.

The following includes definitions of various terms and phrases used throughout this specification.

The terms "about" or "approximately" are defined as being close to as understood by one of ordinary skill in the art. In one non-limiting embodiment, the terms are defined to be within 10%, preferably within 5%, more preferably within 1%, and most preferably within 0.5%.

The terms "wt. %," "vol. %," or "mol. %" refers to a weight percentage of a component, a volume percentage of a component, or molar percentage of a component, respectively, based on the total weight, the total volume of material, or total moles, that includes the component. In a non-limiting example, 10 grams of component in 100 grams of the material is 10 wt. % of component.

The term "substantially" and its variations are defined to include ranges within 10%, within 5%, within 1%, or within 0.5%.

The terms "inhibiting" or "reducing" or "preventing" or "avoiding" or any variation of these terms, when used in the claims and/or the specification includes any measurable decrease or complete inhibition to achieve a desired result.

The term "effective," as that term is used in the specification and/or claims, means adequate to accomplish a desired, expected, or intended result.

The use of the words "a" or "an" when used in conjunction with any of the terms "comprising," "including," "containing," or "having" in the claims, or the specification, may mean "one," but it is also consistent with the meaning of "one or more," "at least one," and "one or more than one."

The phrase "and/or" means and or or. To illustrate, A, B, and/or C includes: A alone, B alone, C alone, a combination of A and B, a combination of A and C, a combination of B and C, or a combination of A, B, and C. In other words, "and/or" operates as an inclusive or.

The words "comprising" (and any form of comprising, such as "comprise" and "comprises"), "having" (and any form of having, such as "have" and "has"), "including" (and any form of including, such as "includes" and "include") or "containing" (and any form of containing, such as "contains" and "contain") are inclusive or open-ended and do not exclude additional, unrecited elements or method steps.

The process and systems of the present invention can "comprise," "consist essentially of," or "consist of" particular ingredients, components, compositions, steps, etc. disclosed throughout the specification. With respect to the transitional phrase "consisting essentially of," in one non-limiting aspect, a basic and novel characteristic of the processes and the systems of the present invention are their abilities for steam cracking a hydrocarbon feed by preheating the hydrocarbon feed with a heated quench water produced from quenching a steam cracking reaction.

Other objects, features and advantages of the present invention will become apparent from the following figures, detailed description, and examples. It should be understood, however, that the figures, detailed description, and examples, while indicating specific embodiments of the invention, are given by way of illustration only and are not meant to be limiting. Additionally, it is contemplated that changes and modifications within the spirit and scope of the invention will become apparent to those skilled in the art from this detailed description. In further embodiments, features from specific embodiments may be combined with features from other embodiments. For example, features from one embodiment may be combined with features from any of the other embodiments. In further embodiments, additional features may be added to the specific embodiments described herein.

BRIEF DESCRIPTION OF THE DRAWINGS

Advantages of the present invention may become apparent to those skilled in the art with the benefit of the following detailed description and upon reference to the accompanying drawings.

Figure 1A:
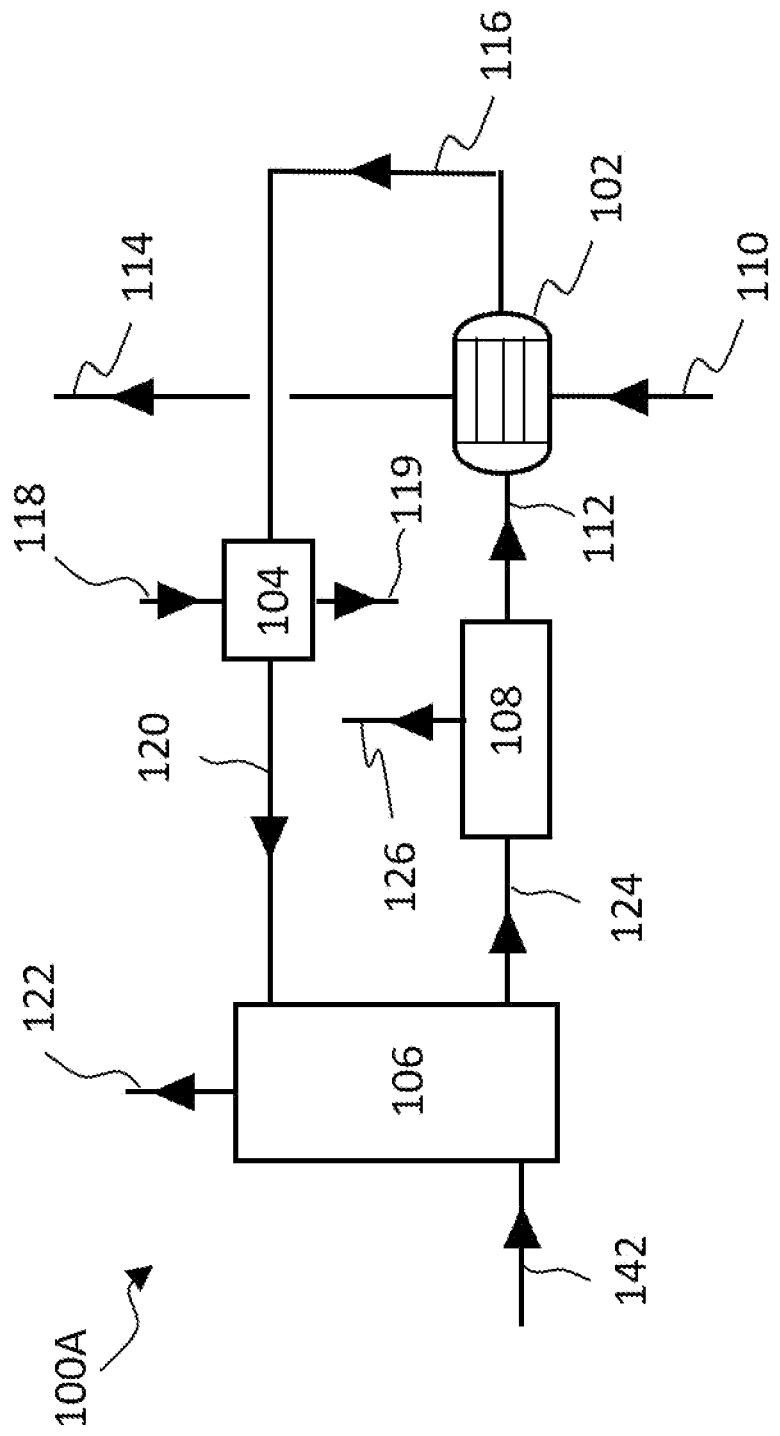
FIG. 1A is a schematic of an example of the present invention for heating a hydrocarbon feed for steam cracking.

While the invention is susceptible to various modifications and alternative forms, specific embodiments thereof are shown by way of example in the drawings. The drawings may not be to scale.

DETAILED DESCRIPTION OF THE INVENTION

A discovery has been made that provides a solution to the high energy costs involved in steam cracking of hydrocarbons. The solution can include using heat energy produced in a process step of the steam cracking process to provide for the heat energy required for another process step of the steam cracking process, such that use of external heat energy for the second process step and overall steam cracking process can be reduced. In particular, the solution can include pre-heating a hydrocarbon feed for steam cracking by heat exchange with a heated quench water produced from quenching a steam cracking reaction.

These and other non-limiting aspects of the present invention are discussed in further detail in the following paragraphs with reference to the figures.

Referring to FIG. 1A, one example of the system and process of the present invention for heating a hydrocarbon feed for a steam cracking reaction is described. System 100A can include a first heat exchanger 102, a quench water cooler 104, a quench water tower (QWT) 106 and a quench water separator drum (QWSD) 108. A hydrocarbon feed stream 110 and a first quench water stream 112 can be fed to the first heat exchanger 102. In the first heat exchanger 102 the hydrocarbon feed stream 110 can be heated with the first quench water stream 112 by heat exchange with or without direct contact to form a heated hydrocarbon feed stream 114, and the first quench water stream 112 can get cooled by the heat exchange process to form a second quench water stream 116. The heated hydrocarbon feed stream 114 can have a temperature higher than the hydrocarbon feed stream 110. The second quench water stream 116 can have a temperature lower than the first quench water stream 112. The heated hydrocarbon feed stream 114 can be fed to a cracking furnace (not shown). The second quench water stream 116 can be fed to a quench water cooler 104. In the quench water cooler 104 the second quench water stream 116 can get further cooled by a cold water stream 118 by heat exchange with or without direct contact to form a quench water stream 120, and the cold water stream 118 can get heated by the heat exchange process to form the stream 119. The quench water stream 120 can have a temperature lower than the second water stream 116. The quench water stream 120 from the quench water cooler 104 can be fed to the QWT 106. In other embodiments, the second quench water stream 116 can be fed directly to the QWT 106 (not shown). A cracked stream 142 containing cracked gases, e.g. hot cracked gases from a cracking furnace (not shown) can be fed to the QWT 106. In the QWT 106 the cracked stream 142 can be contacted with the quench water stream 120, to form a gaseous stream 122 containing quenched cracked gases (e.g., ethylene, propylene, butylene, etc., or any combination thereof, preferably the quenched cracked gases include at least ethylene) and a crude water stream 124 containing heated quench water. The crude water stream 124 containing the heated quench water can enter the QWSD 108 from the QWT 106. In QWSD 108 the crude water stream can be separated to form the first quench water stream 112. The first quench water stream 112 can contain the heated quench water. In some aspects, the crude water stream 124 can further contain condensed and/or liquid hydrocarbons and in the QWSD 108 the heated quench water can be separated from the condensed and/or liquid hydrocarbons to form the first quench water stream 112. In some aspects, the condensed and/or liquid hydrocarbons can contain pyrolysis gasoline, and a stream 126 containing at least a portion of the pyrolysis gasoline separated from the heated quench water can exit the QWSD 108. The stream 126 containing pyrolysis gasoline can be subjected to further process steps (not shown). The arrows indicate the overall flow direction of the respective streams.

Figure 1B:
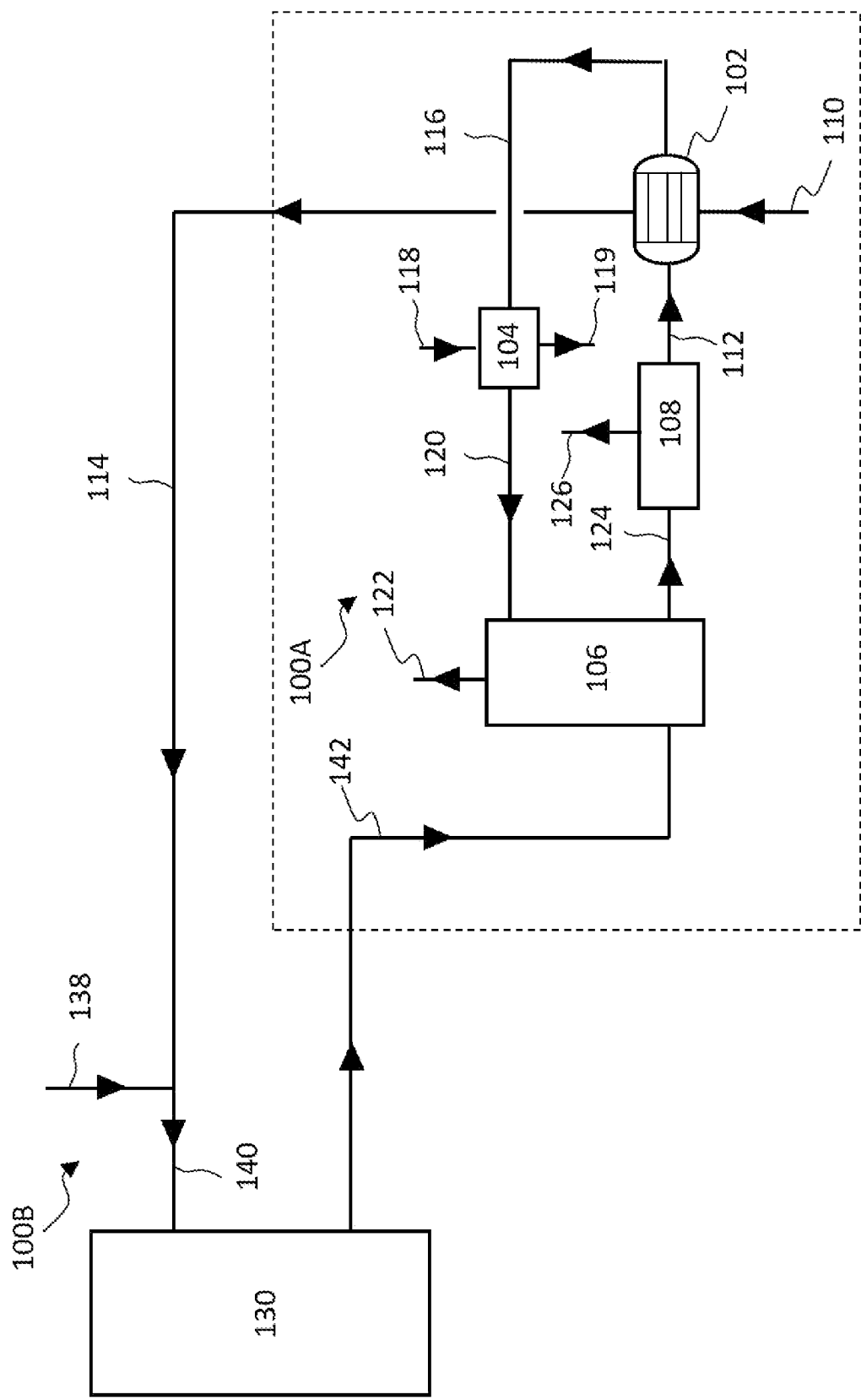
FIG. 1B is a schematic of an example of the present invention for steam cracking of a hydrocarbon feed.

Referring to FIG. 1B, an example of the system and process of the present invention for steam cracking is described. System 100B can include the system 100A of FIG. 1 and a cracking furnace 130. The hydrocarbon feed of the system 100B can be heated using system 100A. The heated hydrocarbon feed stream 114 obtained from heating the hydrocarbon feed stream 110, can be contacted with a dilution steam stream 138 to form a mixed stream 140. The mixed stream can be fed to the cracking furnace 130 and can be cracked to form the cracked stream 142 containing cracked gases, e.g. hot cracked gases. In some aspects, the heated hydrocarbon feed stream prior to contacting with the dilution steam stream can be fed to a convection section of the cracking furnace and be further heated. The further heated hydrocarbon feed stream can be contacted with the dilution steam stream to form the mixed stream. The cracked stream 142 can be fed to the QWT 106.

Figure 2:
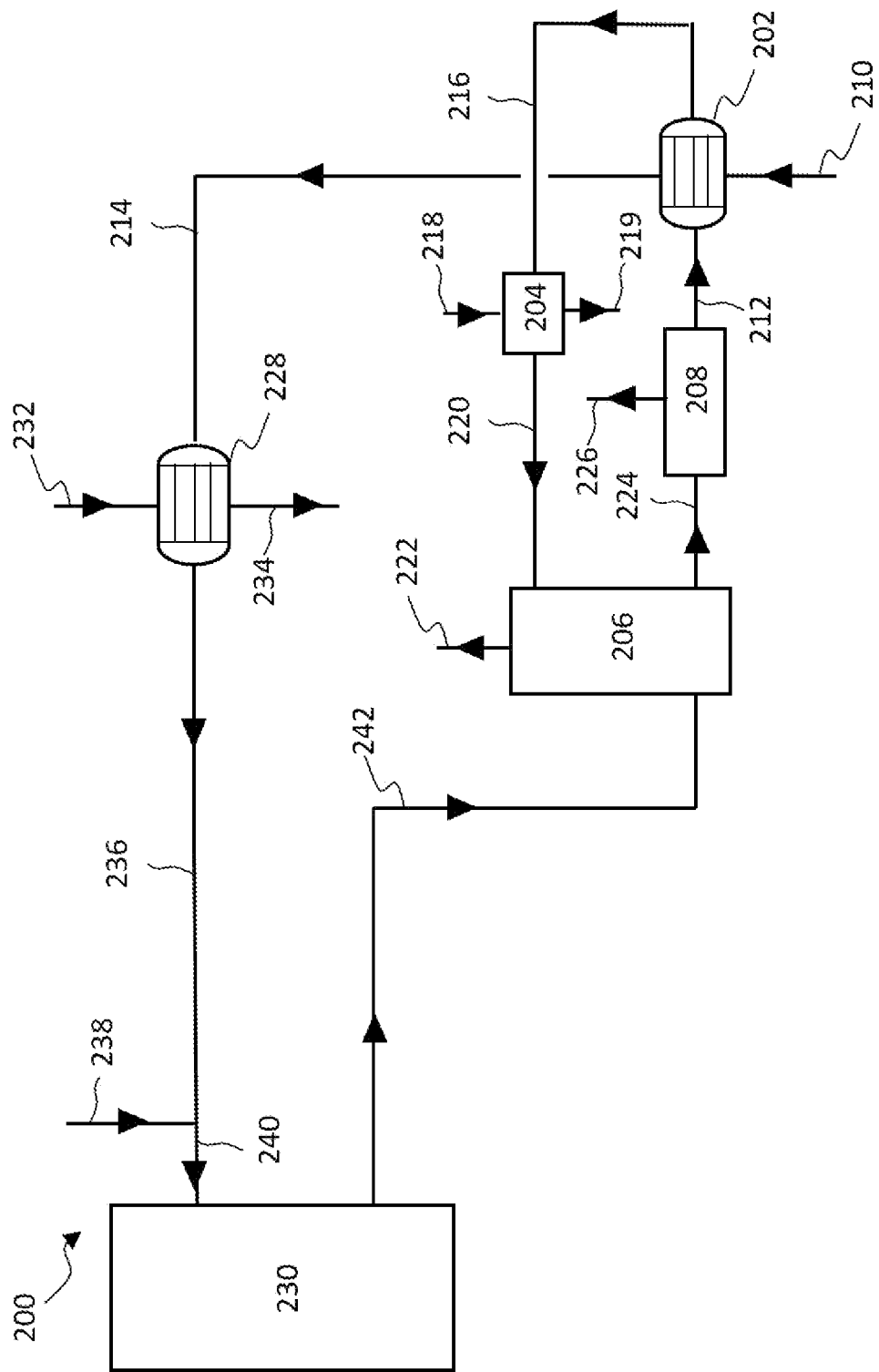
FIG. 2 is a schematic of another example of the present invention for steam cracking of a hydrocarbon feed.

Referring to FIG. 2, an example of the system and process of the present invention for steam cracking is described. System 200 can include, a first heat exchanger 202, a quench water cooler 204, a QWT 206, a QWSD 208, a second heat exchanger 228, and a cracking furnace 230. A hydrocarbon feed stream 210 and a first quench water stream 212 can be fed to the first heat exchanger 202. In the first heat exchanger 202 the hydrocarbon feed stream 210 can be heated with the first quench water stream 212 by heat exchange with or without direct contact to form a heated hydrocarbon feed stream 214, and the first quench water stream 212 can be cooled by the heat exchange process to form a second quench water stream 216. The heated hydrocarbon feed stream 214 can have a temperature higher than the hydrocarbon feed stream 210 and the second quench water stream 216 can have a temperature lower than the first quench water stream 212. The heated hydrocarbon feed stream 214 can be fed to the cracking furnace 230 via the second heat exchanger 228. A low pressure steam stream 232 and the heated hydrocarbon feed stream 214 can be fed to the second heat exchanger 228. In the second heat exchanger 228 the heated hydrocarbon feed stream 214 can be heated with the low pressure steam stream 232 by heat exchange with or without direct contact to form a second heated hydrocarbon feed stream 236, and the low pressure steam stream 232 can be cooled by the heat exchange process to form a stream 234. The second heated hydrocarbon feed stream 236 can have a temperature higher than the heated hydrocarbon feed stream 214 and the low pressure steam stream 232 can have a temperature lower than the stream 234. The second heated hydrocarbon feed stream can be contacted with a dilution steam stream 238 to form a mixed stream 240. The mixed stream can be fed to the cracking furnace 230 and can be cracked to form the cracked stream 242 containing cracked gases, e.g. hot cracked gases. In some aspects, the second heated hydrocarbon feed stream prior to contacting with the dilution steam stream can be fed to a convection section of the cracking furnace and be further heated. The further heated second heated hydrocarbon feed stream can be contacted with the dilution steam stream to form the mixed stream. The cracked stream 242 can be fed to the QWT 206. The second quench water stream 216 from the first heat exchanger 202 can be fed to the quench water cooler 204. In the quench water cooler 204 the second quench water stream 216 can get further cooled by a cold water stream 218 by heat exchange with or without direct contact to form a quench water stream 220, and the cold water stream 218 can be heated by the heat exchange process to form the stream 219. The quench water stream 220 can have a temperature lower than the second quench water stream 216. The quench water stream 220 from the quench water cooler 204 can be fed to the QWT 206. In the QWT 206 the cracked stream 242 can be contacted with the quench water stream 220, to form a gaseous stream 222 containing quenched cracked gases (e.g., ethylene, propylene, butylene, etc., or any combination thereof, preferably at least ethylene) and a crude water stream 224 containing heated quench water. The crude water stream 224 containing the heated quench water can enter the QWSD 208 from the QWT 206. In quench water separator 208 the crude water stream can be separated to from the first quench water stream containing the heated quench water. In some aspects, the crude water stream can further contain condensed and/or liquid hydrocarbons and in the QWSD 208 heated quench water can be separated from at least a portion of the condensed and/or liquid hydrocarbons to form the first quench water stream. In some aspects, the condensed and/or liquid hydrocarbons can contain pyrolysis gasoline, and a stream 226 containing at least a portion of the pyrolysis gasoline separated from the heated quench water, can exit the QWSD 208. The steam 226 containing pyrolysis gasoline can be subjected to further process steps (not shown). The arrows indicate the overall flow direction of the respective streams.

Figure 3:
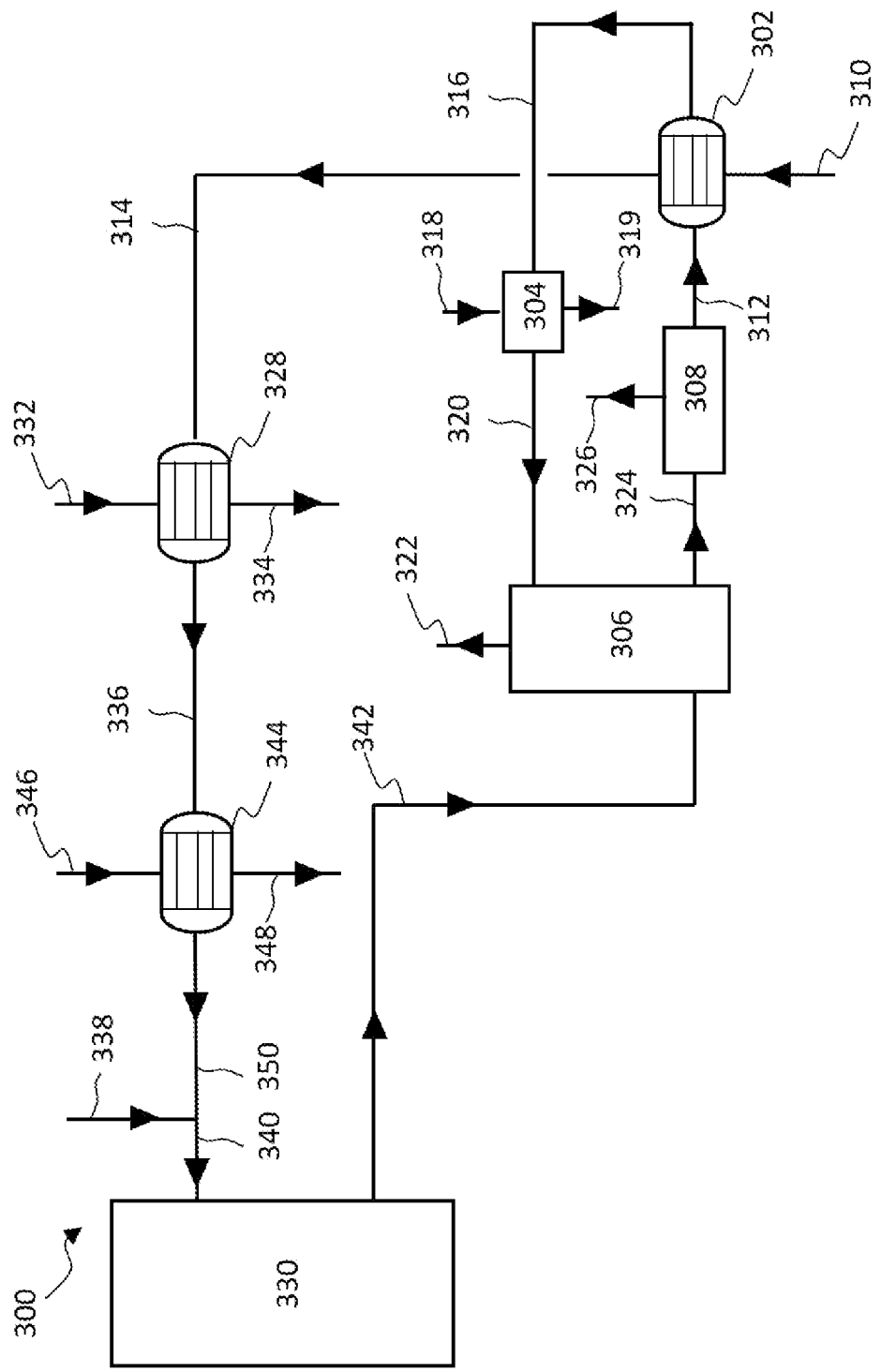
FIG. 3 is a schematic of another example of the present invention for steam cracking of a hydrocarbon feed.

Referring to FIG. 3, another example of the system and process of the present invention for steam cracking is described. System 300 can include, a first heat exchanger 302, a quench water cooler 304, a QWT 306, a QWSD 308, a second heat exchanger 328, a third heat exchanger 344 and a cracking furnace 330. The first heat exchanger 302, the quench water cooler 304, the QWT 306, and the QWSD 308 of the system 300 can be configured similarly to the first heat exchanger 202, the quench water cooler 204, the QWT 206, and the QWSD 308 respectively of the system 200. The hydrocarbon feed stream 310, first quench water stream 312, second quench water stream 316, cold water stream 318, stream 319, quench water stream 320, stream containing quenched cracked gases 322, crude water stream 324 and stream containing pyrolysis gasoline 326 of the system 300 can be configured similarly to the hydrocarbon feed stream 210, first quench water stream 212, second quench water stream 216, cold water stream 218, stream 219, quench water stream 220, stream containing quenched cracked gases 222, crude water stream 224 and stream containing pyrolysis gasoline 226 respectively of the system 200. In system 300, the heated hydrocarbon feed stream 314 from the first heat exchanger can be fed to the cracking furnace 330 via the second heat exchanger 328 and the third heat exchanger 344. A low pressure steam stream 332 and the heated hydrocarbon feed stream 314 can be fed to the second heat exchanger 328. In the second heat exchanger 328 the heated hydrocarbon feed stream 314 can be heated with the low pressure steam stream 332 by heat exchange with or without direct contact to form a second heated hydrocarbon feed stream 336, and the low pressure steam 332 can get cooled by the heat exchange process to form a stream 334. The second heated hydrocarbon feed stream 336 can have a temperature higher than the heated hydrocarbon feed stream 314. A high pressure steam stream 346 and the second heated hydrocarbon feed stream 336 can be fed to the third heat exchanger 344. In the third heat exchanger 344 the second heated hydrocarbon feed stream 336 can be heated with the high pressure steam stream 346 by heat exchange with or without direct contact to form a third heated hydrocarbon feed stream 350, and the high pressure steam stream 346 can get cooled by the heat exchange process to form a stream 348. The third heated hydrocarbon feed stream 350 can have a temperature higher than the second heated hydrocarbon feed stream 336. The third heated hydrocarbon feed stream 350 can be contacted with a dilution steam stream 338 to form a mixed stream 340. The mixed stream 340 can be fed to the cracking furnace 330 and can get cracked to form the cracked stream 342 containing cracked gases e.g. hot cracked gases. In some aspects, the third heated hydrocarbon feed stream prior to contacting with the dilution steam stream can be fed to a convection section of the cracking furnace and get further heated. The further heated third heated hydrocarbon feed stream can be contacted with the dilution steam stream to form the mixed stream. The cracked stream 342 can be fed to the QWT 306. The arrows indicate the overall flow direction of the respective streams.

The hydrocarbon feed stream 110, 210, 310 can contain a hydrocarbon feed for steam cracking. In some aspects, the hydrocarbon feed can contain naphtha, liquid petroleum gas (LPG), ethane, or propane or any combination thereof. At least a portion of the hydrocarbon feed from the hydrocarbon feed stream can be fed to the cracking furnace, via the heated hydrocarbon feed stream (system 100B), or the heated hydrocarbon feed stream and the second heated hydrocarbon feed stream (system 200), or the heated hydrocarbon feed stream, the second heated hydrocarbon feed stream and the third heated hydrocarbon feed stream (system 300). The hydrocarbon feed stream 110, 210, 310 can have a temperature of from 5 to 80° C., preferably from 15° C. to 80° C., or more preferably from 5° C. to 40° C. In the first heat exchanger 102, 202, 302 the hydrocarbon feed stream 110, 210, 310 can get heated by heat transfer from the first quench water stream 112, 212, 312 to form the heated hydrocarbon feed stream 114, 214, 314. The first heat exchanger 110, 210, 310 can be a heat exchanger known in the art. At least a portion of the hydrocarbon feed from the hydrocarbon feed stream 110, 210, 310 can get transferred, e.g. carried over to the heated hydrocarbon feed stream 114, 214, 314. The heated hydrocarbon feed stream can have a temperature of, such as at an outlet of the stream at the first heat exchanger 70° C. to 100° C. or at least any one of, equal to any one of, or between any two of 70, 75, 80, 85, 90, 95 and 100° C., and preferably between 70° C. and 80° C. The temperature of the heated hydrocarbon feed stream at its outlet at the first heat exchanger can be 5° C. to 85° C. higher or at least any one of, equal to any one of, or between any two of 5, 15, 25, 35, 45, 55, 65, 75, and 85° C. higher than the temperature of the hydrocarbon feed stream at its inlet at the first heat exchanger and preferably from 40° C. to 75° C. higher.

In the second heat exchanger 228, 328 the heated hydrocarbon feed stream 214, 314 can get heated by heat transfer from the low pressure steam stream 232, 332 to form the second heated hydrocarbon feed stream 236, 336. The second heat exchanger 228, 328 can be a heat exchanger known in the art. The low pressure steam stream 232, 332 can contain a low pressure steam. The low pressure steam can have a temperature of 220° C. to 280° C. The low pressure steam can have a pressure of 0.1 MPa to 2 MPa, and preferably from 0.35 MPa to 0.45 MPa or at least any one of, equal to any one of, or between any two of 0.1, 0.2, 0.3, 0.4, 0.5, 0.6, 0.7, 0.8, 0.9, 1, 1.1, 1.2, 1.3, 1.4, 1.5, 1.6, 1.7, 1.8, 1.9 and 2 MPa. At least a portion of the hydrocarbon feed from the heated hydrocarbon feed stream 214, 314 can get transferred e.g. carried over to the second heated hydrocarbon feed stream 236, 336. The second heated hydrocarbon feed stream can have a temperature of, such as at an outlet of the stream at the second heat exchanger 100 to 200° C., and preferably from 125° C. to 130° C., or at least any one of, equal to any one of, or between any two of 100, 110, 120, 130, 140, 150, 160, 170, 180, 190, 200, 210, 220, 230, 240 and 250° C. The temperature of the second heated hydrocarbon feed stream at its outlet at the second heat exchanger can be 5° C. to 150° C. higher, and preferably from 50° C. to 60° C. higher or at least any one of, equal to any one of, or between any two of 5, 10, 20, 30, 40, 50, 60, 70, 80, 90, 100, 110, 120, 130, 140 and 150° C. higher than the temperature of the heated hydrocarbon feed stream at its inlet at the second heat exchanger.

In the third heat exchanger 344 the second heated hydrocarbon feed stream 336 can get heated by heat transfer from the high pressure steam stream 346 to form the third heated hydrocarbon feed stream 350. The third heat exchanger 344 can be a heat exchanger known in the art. The high pressure steam stream 346 can contain high pressure steam. The high pressure steam can have a temperature of 370° C. to 390° C., and a pressure of 1.5 to 5 MPa, preferably from 4 MPa to 4.5 MPa, or at least any one of, equal to any one of, or between any two of 1.5, 2, 2.5, 3, 3.5, 4, 4.5 and 5 MPa. At least a portion of the hydrocarbon feed from the second heated hydrocarbon feed stream 336 can get transferred i.e. carried over to the third heated hydrocarbon feed stream 350. The third heated hydrocarbon feed stream can have a temperature of, such as at an outlet of the stream at the third heat exchanger 200 to 400° C., and preferably from 135° C. to 145° C. or at least any one of, equal to any one of, or between any two of 200, 210, 220, 230, 240, 250, 260, 270, 280, 290, 300, 310, 320, 330, 340, 350, 360, 370, 380, 390, and 400° C. The temperature of the third heated hydrocarbon feed stream at its outlet at the third heat exchanger can be 5 to 200° C. higher, and preferably from 10° C. to 20° C. higher or at least any one of, equal to any one of, or between any two of 5, 10, 20, 30, 40, 50, 60, 70, 80, 90, 100, 110, 120, 130, 140, 150, 160, 170, 180, 190 and 200° C. higher than the temperature of the second heated hydrocarbon feed stream at its inlet at the third heat exchanger.

The dilution steam stream 138, 238, 338 can contain dilution steam. Dilution steam can be mixed with the hydrocarbon feed for steam cracking to reduce hydrocarbon partial pressure and increase olefin yield from steam cracking. The mixed stream 140, 240, 340 can contain steam i.e. dilution steam from the dilution steam stream 238, 338 and the hydrocarbon feed from the feed stream 114, 236, 350. The hydrocarbon to steam weight ratio in the mixed stream 140, 240, 340 can be 0.3 to 0.4. The mixed stream 140, 240, 340 can be fed to the cracking furnace 130, 230, 330 and the hydrocarbon feed can be steam cracked in the cracking furnace 130, 230, 330.

The cracking furnace 130, 230, 330 can be a cracking furnace known in the art. In the cracking furnace 130, 230, 330 the hydrocarbon feed in presence of steam i.e. dilution steam can be cracked by heating at a temperature 700 to 1000° C., and preferably from 820° C. to 900° C. or at least any one of, equal to any one of, or between any two of 700, 710, 720, 730, 740, 750, 760, 770, 780, 790, 800, 810, 820, 830, 840, 850, 860, 870, 880, 890, 900, 910, 920, 930, 940, 950, 960, 970, 980, 990 and 1000° C. and/or pressure 0.05 to 0.1 MPa. In some aspects, the cracking furnace can have a convection zone and a radiation zone and, the mixed stream can get preheated in the convection zone and/or steam cracking of the mixed stream can be performed in the radiation zone. The cracked stream 142, 242, 342 produced by steam cracking of the hydrocarbon feed in the cracking furnace 130, 230, 330 can contain cracked gases i.e. hot cracked gases.

The cracked stream 142, 242, 342 is quenched to reduce undesired reactions and optimize desired products, such as olefins yield. The cracked stream 142, 242, 342 can be quenched in the QWT 106, 206, 306 by contacting the cracked stream 142, 242, 342 with the quench water stream 120, 220, 320. The quench water stream can contain quench water i.e. cold quench water. The quench water stream i.e. the cold quench water can have a temperature of, such as at an inlet of the stream at the QWT 20 to 70° C., and preferably from 35° C. to 42° C., or at least any one of, equal to any one of, or between any two of 20, 25, 30, 35, 40, 45, 50, 55, 60, 65 and 70° C. In the QWT 106, 206, 306 the cracked gases of the cracked stream can contact, the quench water of the quench water stream and can get cooled to form quenched cracked gases. The quench water in the process can get heated to form heated quench water. The quenched cracked gases can exit the QWT 106, 206, 306 via the stream 122, 222, 322. The quenched cracked gases can contain olefins such as ethylene, propylene and/or butylene. The stream 122, 222, 322 can be subjected to further process steps such as one or more compression, drying and/or separation steps to obtain polymer grade olefins, such as polymer grade ethylene, propylene and/or butylene. The heated quench water can exit the QWT 106, 206, 306 via the crude water stream 124, 224, 324. The crude water stream in addition to the heated quench water can contain condensed and/or liquid hydrocarbons. In some aspects, the condensed and/or liquid hydrocarbons can contain pyrolysis gasoline and/or tar. The condensed and/or liquid hydrocarbons can be water miscible or immiscible and can be present in the crude water stream as water dissolved hydrocarbons, water-hydrocarbon emulsion and/or separate hydrocarbon phase.

At least a portion of the condensed and/or liquid hydrocarbons can be separated from the heated quench water in QWSD 108, 208, 308. The QWSD 108, 208, 308 can be a QWSD known in the art. In some aspects, the pyrolysis gasoline can migrate to a top portion of the QWSD 108, 208, 308 and can be removed via the stream 126, 226, 336. The first quench water stream 112 can contain the separated heated quench water from the QWSD 108, 208, 308. The first quench water stream 112, 212, 312 i.e. the heated quench water in the first quench water stream can have a temperature of, such as at an inlet of the stream at the first heat exchanger 70° C. to 120° C., and preferably from 76° C. to 84° C. or at least any one of, equal to any one of, or between any two of 70, 75, 80, 85, 90, 95, 100, 105, 110, 115 and 120° C.

In the first heat exchanger 102, 202, 302 heat from the heated quench water of the first quench water stream 112, 212, 312 can get transferred to the hydrocarbon feed in the hydrocarbon feed stream 110, 210, 310 to form a partially cooled quench water. The second quench water stream 116, 216, 316 can contain the partially cooled quench water. The second quench water stream 112, 212, 312 i.e. the partially cooled quench water in the second quench water stream can have a temperature of, such as at an outlet of the stream at the first heat exchanger 50 to 100° C., and preferably from 78° C. to 83.5° C. or at least any one of, equal to any one of, or between any two of 50, 55, 60, 65, 70, 75, 80, 85, 90, 95, and 100° C. The temperature of the second quench water stream at its outlet at the first heat exchanger can be 0.5 to 70° C., preferably from 5 to 70° C., and more preferably from 0.5° C. to 1.5° C. lower or at least any one of, equal to any one of, or between any two of 5, 10, 15, 20, 25, 30, 35, 40, 45, 50, 55, 60, 65 and 70° C. lower than temperature of the first quench water stream at its inlet at the first heat exchanger.

In the quench water cooler 104, 204, 304 the partially cooled quench water in the second quench water stream 116, 216, 316 can further get cooled by heat transfer to the cold water stream 118, 218, 318, to a form the quench water i.e. cold quench water. Quench water cooler 104, 204, 304 can be a quench water cooler, such as a heat exchanger known in the art. The quench water stream 120, 220, 320 can contain the quench water from the quench water cooler 104, 204, 304.

In FIGS. 1-3 the reactors, units and/or zones can include one or more heating and/or cooling devices (e.g., insulation, electrical heaters, jacketed heat exchangers in the wall) and/or controllers (e.g., computers, flow valves, automated values, etc.) that can be used to control the process temperature and pressure of the process. While only one unit or zone is shown, it should be understood that multiple reactors or zones can be housed in one unit or a plurality of units or reactors housed in one unit.

Although embodiments of the present application and their advantages have been described in detail, it should be understood that various changes, substitutions and alterations can be made herein without departing from the spirit and scope of the embodiments as defined by the appended claims. Moreover, the scope of the present application is not intended to be limited to the particular embodiments of the process, machine, manufacture, composition of matter, means, methods and steps described in the specification. As one of ordinary skill in the art will readily appreciate from the above disclosure, processes, machines, manufacture, compositions of matter, means, methods, or steps, presently existing or later to be developed that perform substantially the same function or achieve substantially the same result as the corresponding embodiments described herein can be utilized. Accordingly, the appended claims are intended to include within their scope such processes, machines, manufacture, compositions of matter, means, methods, or steps.

EXAMPLE 1

Steam Cracking of Ethane

Simulations of the steam cracking process of ethane was performed. Two parallel simulations were run. In a comparative process, process one, a hydrocarbon feed stream containing ethane was not heated with quench water. In a process according to an example of the current invention, process two, a hydrocarbon feed stream containing ethane was heated with quench water. It was found the steam consumption in process two was 7% less compared to process one. Thus, the process according to an example of the current invention is more energy efficient than the comparative process.

The invention claimed is:

1. A method for steam cracking of hydrocarbons, the method comprising:
   (a) heating a hydrocarbon feed stream with a first quench water stream to form a heated hydrocarbon feed stream and a second quench water stream having a temperature lower than the first quench water stream;
   (b) steam cracking the heated hydrocarbon feed stream to form a cracked stream comprising cracked gases;
   (c) contacting the cracked stream with quench water to form a gaseous stream comprising quenched cracked gases and a crude water stream comprising heated quench water and pyrolysis gasoline; and
   (d) separating the crude water stream to form the first quench water stream.

2. The method of claim 1, wherein the method further comprises, prior to steam cracking, heating the heated hydrocarbon feed stream with a low pressure steam stream to form a second heated hydrocarbon feed stream and the second heated hydrocarbon feed stream is steam cracked in step (b).

3. The method of claim 2, wherein the low pressure steam stream has a pressure of 0.35 MPa to 0.45 MPa, and/or temperature of 220° C. to 280° C.

4. The method of claim 2, wherein the second heated hydrocarbon feed stream has a temperature of 125° C. to 130° C.

5. The method of claim 2, wherein the heated hydrocarbon feed stream is heated with the low pressure steam stream by heat exchange with and/or without direct contact.

6. The method of claim 2, wherein the method further comprises, prior to steam cracking, heating the second heated hydrocarbon feed stream with a high pressure steam stream to form a third heated hydrocarbon feed stream and the third heated hydrocarbon feed stream is steam cracked in step (b).

7. The method of claim 6, wherein the high pressure steam stream has a pressure of 4 MPa to 4.5 MPa, and/or temperature of 370° C. to 390° C.

8. The method of claim 6, wherein the third heated hydrocarbon feed stream has a temperature of 135° C. to 145° C.

9. The method of claim 6, wherein the second heated hydrocarbon feed stream is heated with the high pressure steam stream by heat exchange with and/or without direct contact.

10. The method of claim 1, wherein the heated hydrocarbon feed stream or second heated hydrocarbon feed stream or the third heated hydrocarbon feed stream is contacted with a dilution steam stream to form a mixed stream and the mixed stream is cracked in step (b).

11. The method of claim 1, wherein the first quench water stream has a temperature of 76° C. to 84° C.

12. The method of claim 1, wherein the heated hydrocarbon feed stream has a temperature of 5° C. to 40° C.

13. The method of claim 1, wherein the second quench water stream has a temperature of 78° C. to 83.5° C.

14. The method of claim 1, wherein the second quench water stream is cooled with a quench water cooler to form the quench water.

15. The method of claim 1, wherein the quench water has a temperature of 35° C. to 42° C.

16. The method of claim 1, wherein the hydrocarbon feed stream is heated with the first quench water stream by heat exchange with and/or without direct contact.

17. The method of claim 1, wherein the cracked stream is contacted with the quench water in a quench water tower.

18. The method of claim 1, wherein the crude water stream is separated in a quench water separator.

19. The method of claim 1, wherein the steam cracking is performed at a temperature of 820° C. to 900° C., and/or a pressure of 0.05 MPa to 0.1 MPa.

20. The method of claim 1, wherein the hydrocarbon feed stream comprises naphtha, liquid petroleum gas, ethane, or propane or any combination thereof.

* * * * *